United States Patent [19]

Westley

[11] 4,129,580

[45] Dec. 12, 1978

[54] RESOLUTION OF CERTAIN ASYMMETRIC PRIMARY AMINES USING LASALOCID

[75] Inventor: John Westley, Cedar Grove, N.J.

[73] Assignee: Hoffmann-La Roche Inc., Nutley, N.J.

[21] Appl. No.: 851,317

[22] Filed: Nov. 14, 1977

Related U.S. Application Data

[63] Continuation-in-part of Ser. No. 708,655, Jul. 26, 1976, abandoned.

[51] Int. Cl.$^2$ .................... C07D 307/22; C07C 85/26
[52] U.S. Cl. ......................... 260/347.7; 260/345.7 R; 260/563 R; 260/570.5 R; 260/570.8 R; 260/570.9; 260/583 N; 260/583 R
[58] Field of Search ......... 260/347.7, 563 R, 570.5 R, 260/570.8 R, 570.9, 583 R, DIG. 8

[56] References Cited

U.S. PATENT DOCUMENTS 3,715,372   2/1973   Stempel et al. .................. 260/345.8

Primary Examiner—Henry R. Jiles
Assistant Examiner—Bernard Dentz
Attorney, Agent, or Firm—Jon S. Saxe; Bernard S. Leon; William M. Farley

[57] ABSTRACT

Racemic modifications of optically active primary or tertiary amines are treated with lasalocid to form diastereomeric salts. The so-formed diastereomeric salts are separated and, subsequently, can be chemically decomposed to give the desired enantiomers of the amine. The resolving agent, lasalocid, is recovered in this process by precipitation or evaporation from organic solvents.

7 Claims, No Drawings

RESOLUTION OF CERTAIN ASYMMETRIC PRIMARY AMINES USING LASALOCID

RELATED APPLICATION

This application is a continuation-in-part of U.S. patent application Ser. No. 708,655, filed July 26, 1976 and now abandoned.

BACKGROUND OF THE INVENTION

Organic primary or tertiary amines which contain a chiral center are usually prepared by synthetic methods which result in a racemic form of the compound. Frequently, biological properties of such compounds are associated primarily, and in some cases exclusively, with one of the possible enantiomers and, therefore, it is desirable and often necessary to resolve the racemate.

A frequently used method, among the known procedures for resolving racemates, employs the difference in properties between the diastereomeric salts obtained upon reaction of a racemic base with an optically active acid. Such procedure comprises mixing the racemate, in an appropriate solvent, with an optically active acid to form diastereomer salts; separating the diastereomers; and decomposing the separated salts to obtain the desired optical isomers of the racemic base.

There is a need for a resolving agent which (a) is suitable for use with the primary and tertiary asymmetric amines, and, particularly, primary and tertiary amines wherein the asymmetric carbon atom is attached directly to the amino group, (b) can be utilized in commercial processes, (c) can be regenerated economically and (d) can be reused.

Several optically active acids are widely employed in industry for this purpose, e.g., camphorsulfonic acid and tartaric acid. The recovery of the aforesaid resolving agents presents an economic problem since these agents are soluble in water and are, thus, difficult to recover. Thus, recycling operations are precluded, necessitating the use of fresh resolving agent for each run. Furthermore, the known resolving agents have limited applicability.

Another resolving agent of wide applicability which meets the desired criteria stated above is (−)-di-O-isopropylidene-2-keto-L-gulonic acid.

SUMMARY OF THE INVENTION

The present invention relates to the use of a polyether antibiotic, lasalocid, as a resolving agent for primary and tertiary asymmetric amines.

This invention particularly relates to processes whereby lasalocid, a polyether antibiotic, is reacted with a racemic mixture of an optically active primary or tertiary amine to form novel diastereomeric salts. The novel diastereomers are subsequently isolated, either in crystalline form or in solution, depending on the properties of the desired compound.

For example, the diastereoisomeric salts are resolved by crystallization of the less soluble diastereoisomer salt from a suitable organic solvent. After filtration, this enantiomer of the amine can then be isolated as a salt of a mineral acid (e.g., hydrochloric, sulfuric, phosphoric and the like) by dissolving it in a suitable solvent such as methylene chloride and then extracting the amine by shaking the solution with dilute aqueous mineral acid followed by precipitation or lyophilization of the amine salt from the aqueous acid solution. The filtrate from the initial crystallization, containing the more soluble diastereoisomeric salt, can also be treated with a dilute aqueous mineral acid to extract the amine followed by precipitation or lyophilization of the amine acid salt from this aqueous acid solution.

The lasalocid, which can be readily recovered from organic halogenated or ester solvents after removal of the resolved amine, then can be used again for subsequent resolution of racemic mixtures of other primary or tertiary asymmetric amines.

DETAILED DESCRIPTION OF THE INVENTION

The products formed according to this invention are salts of lasalocid with the enantiomers of racemic mixtures of optically active primary or tertiary amines. Lasalocid has been found to be an effective resolving agent for primary or tertiary asymmetric amines where the asymmetric carbon atom is either attached to, or separated by one methylene unit from, the primary or tertiary amino group. The preferred primary and tertiary asymmetric amines useful in this invention are those in which one enantiomer is preferentially crystallized as its lasalocid salt.

Thus, lasalocid is a resolving agent for a broad spectrum of organic primary or tertiary amines.

The amines suitable for forming salts with lasalocid, i.e., primary or tertiary amines containing at least one asymmetric center, are those represented by the general formula:

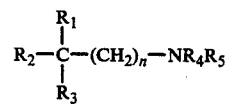

wherein the $R_1$, $R_2$ and $R_3$ moieties can be hydrogen, alkyl, alkenyl, alkynyl, aryl, aralkyl, heterocyclic, alicyclic, hydroxyl, halogen, alkoxy, polyfluoroalkyl and the like; $R_4$ and $R_5$ are either both hydrogen or $R_4$ and $R_5$ can be alkyl, cycloalkyl or cyclic amino and n is an integer from 0 to 1 with the proviso that $R_1$, $R_2$ and $R_3$ cannot be the same moiety.

As used herein, the term "aryl" refers to an aromatic hydrocarbon, such as phenyl or naphthyl radicals having one or more alkyl, alkenyl, alkynyl, alkoxy or halo-lower alkoxy substituents thereon. The term "cycloalkyl" refers to saturated ring systems containing from 3 to 7 carbon atoms.

The term "cyclic amine" means a ring system of 4 to 10 atoms which is heterocyclic in nature; and which contains an amine group. As used herein, such a ring system may be a monocyclic or polycyclic ring, i.e., containing two or more rings produced by fusing other ring systems with the cyclic amine. In such a ring system for asymmetric tertiary amines include those in which two or all three of the nitrogen substituents belong to the same heterocyclic ring. Compounds of this type include:

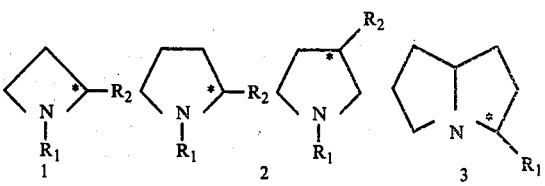

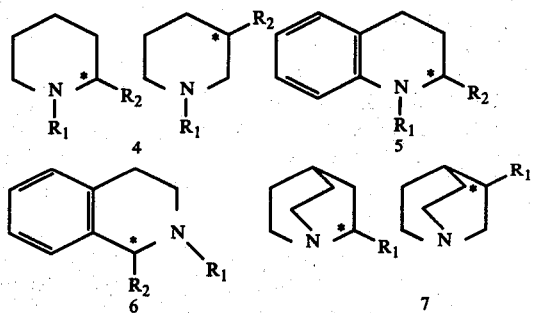

wherein the asymmetric carbon atom is indicated by * and wherein $R_1$ and $R_2$ are alkyl, aryl or alkylaryl groups.

As depicted above:
1 = Azetidines
2 = Pyrrolidines
3 = Pyrrolizidines
4 = Piperidines
5 = 1,2,3,4-tetrahydroquinolines
6 = 1,2,4-tetrahydroiso-quinolines
7 = quinuclidines Suitable amines include alkyl amines, e.g., 2-aminoheptane; 2-aminobutane, 2-aminopentane, 2-aminohexane, 2-amino-4-methylpentane, 2-amino-4-dimethylpentane, 1-amino-1-cyclohexylethane and the like; aralkyl amines, e.g., 1-amino-1-phenylethane, 1-amino-1-(4-bromophenyl) ethane, 1-dimethylamino-1-phenylethane, 1-amino-1-naphthylethane, 1-amino-2-(3'4'-dimethoxyphenyl) propane and the like and heterocyclic amines, e.g., tetrahydrofurfuryl-amine and the like.

Lasalocid (formerly known as antibiotic X-537A) is a designation for the crystalline material produced by fermentation of Streptomyces X-537, a culture of which is on deposit in the American Type Culture Collection under the designation ATCC 31180.

Lasalocid, 6-{7(R)-[5(S)-ethyl-5-(5(R)-ethyltetrahydro-5-hydroxy-6(S)-methyl-2H-pyran-2(R)-yl]-tetrahydro-3(S)-methyl-2(S)-furyl]-4(S)-hydroxy-3(R), 5(S)-dimethyl-6-oxononyl}-2,3-cresotic acid is represented by the formula

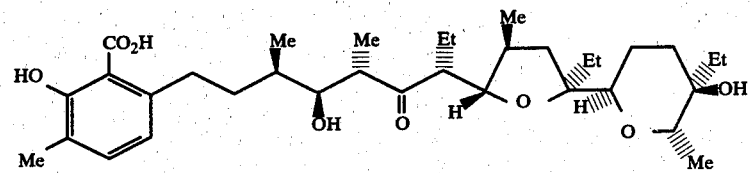

The preparatory procedure for lasalocid and its derivatives is disclosed in U.S. Pat. No. 3,715,372, issued Feb. 6, 1973 and entitled "Derivatives of Antibiotic X-537A" by A. Stempel and J. Westley and also in an article entitled "The Isolation of Three New Crystalline Antibiotics from Streptomyces" by J. Berger et al., J. Amer. Chem. Soc., 73, 5295-98 (1951). Lasalocid is known as an effective coccidiostat.

The nomenclature adopted to define absolute configuration of substituents bound to the asymmetric carbon atom, i.e., the chiral center, of a primary amine is described in the Journal of Organic Chemistry, 34, 2849 (1970) under the title "IUPAC Tentative Rules for the Nomenclature of Organic Chemistry. Section E. Fundamental Stereochemistry". This system of nomenclature is used herein.

The lasalocid amine salts formed according to this invention are useful as intermediates in the resolution of racemic primary or tertiary amines. The optically active amines which are, in turn, prepared from these salts have a variety of uses, e.g., as pharmaceuticals, as resolving agents for racemic asymmetric acids. The thus resolved acids may also have utility as, e.g., pharmaceuticals or intermediates in the preparation of pharmaceuticals.

Generally, the salts of this invention are formed by reacting lasalocid with a racemic primary or tertiary amine in an organic solvent, preferably methylene chloride. This reaction is effected most readily at a temperature of from about 0° C. to preferably room temperature (about 25° C. to 28° C.). The reactants are mixed in about equimolar amounts. The resulting product consists of a mixture of the two optically active forms of the amine as salts of lasalocid. In most cases, at least one of the diastereomeric salts is more readily crystallized and can, thus, be isolated by crystallization from a suitable solvent. However, in the event that the compounds cannot be isolated by crystallization, other techniques, e.g., separation by fractional liquid-liquid extraction or by attachment of lasalocid to a stationary phase and separation by column chromatography, could be employed.

Solvents which are suitable for use in this invention include halogenated organic solvents such as chloroform, carbon tetrachloride, methylene chloride and the like; alcohols such as methanol, ethanol, propanol and the like; esters such as ethyl acetate, butyl acetate and the like; straight or branched chain $C_5$-$C_{10}$ hydrocarbons such as n-hexane, cyclohexane and the like; ethers such as diethyl ether, tetrahydrofuran and the like and other organic solvents such as acetonitrile and dimethylformamide.

The desired enantiomer is finally regenerated from the optically active lasalocid amine salt by chemical means, e.g., by dissolving the diastereoimeric salt in a suitable halogenated organic solvent, e.g., methylene chloride, followed by extraction with dilute aqueous mineral acid, preferably hydrochloric acid, to give the acid salt of the amine. The acid used must be stronger than lasalocid and, for high yields, should be used in excess (i.e., 10-25 fold excess). For example, dilute hydrochloric acid as well as other dilute mineral acids (e.g. hydrobromic, sulfuric, phosphoric, nitric) are suitable. Generally, a concentration of about 0.05-1.5N can be used and reaction temperatures of from about 0° C. to room temperature (about 25° C. to 28° C.) are suitable. The lasalocid remains in the organic solvent until isolated by evaporation of the solvent or by other means.

In the resolution with lasalocid of primary asymmetric amines wherein the asymmetric carbon atom is attached to the primary amine group, the preferential crystalline product yields amines with the R-configuration. In the case of primary amines wherein the asymmetric carbon atom is separated by a methylene unit from the amino group, resolution with lasalocid is more likely to yield, from the preferential crystalline product, an amine having the S-configuration depending, of course, on the nature of the substituents at the asymmetric center. In the case of tertiary asymmetric amines wherein the asymmetric carbon is attached to the tertiary amino group, the diastereoisomeric product that crystallizes preferentially yields amines with the S-configuration. The resolving property of lasalocid with racemic amines resides in the molecular interaction between the anion of the antibiotic and the ammonium cation. As determined by X-ray analysis of the 1-(R)-amino-1-(4-bromophenyl)ethane salt of lasalocid, the ammonium ion is hydrogen bound via three ligands of lasalocid to (1) the carboxyl oxygen (2) the ether oxygen of the central tetrahydrofuranyl ring and (3) the tertiary alcohol on the terminal ring.

The diastereoisomer is therefore a salt-complex rather than a simple ion-pair salt.

The following examples issustrate the invention. All temperatures are 0° C. Of the amines used in the examples, 1-amino-1-phenylethane, 1-amino-1-(4-bromophenyl) ethane, 1-dimethylamino-1-phenylethane, 1-amino-1-naphthylethane, 2-aminoheptane and tetrahydrofurfurylamine are known articles of commerce and are commercially available (e.g., Aldrich Chemical Company and Norse Laboratories). The amine used in Example 1, 1-amino-2-(3',4'-dimethoxyphenyl)-propane is prepared by alkylation of 3,4-dimethoxyphenyl propionitrile with methyl bromide followed by reduction to the amine with Raney cobalt and methanol.

EXAMPLE 1

(a) Optical resolution of racemic 1-amino-2-(3',4'-dimethoxyphenyl)propane 390 mg. (2 mmol.) of racemic 1-amino-2-(3',4'-dimethoxyphenyl) propane, dissolved in 2 ml. of methylene chloride, are admixed with 1.18 g. (2 mmol.) of lasalocid dissolved in 4 ml. of methylene chloride. After 24 ml. of ethanol were added to this mixture, the solution was left at room temperature overnight. As the methylene chloride evaporated, crystals form from the concentrated solution. These crystals are separated by filtration to yield the lasalocid salts of 1-amino-2-(3',4'-dimethoxyphenyl) propane.

The optical purity, and, hence, the degree of discrimination between the enantiomers of the crystalline lasalocid salt of 1-amino-2-(3',4'-dimethoxyphenyl)propane was determined by Gas-Liquid Chromatography (GLC) analysis of its N-trifluoroacetyl-L(S)-prolyl chloride (TPC) derivative. The TPC reagent is commercially available from Regis Chemical Company as a 0.1M solution in $CHCl_3$. The procedure used is described in detail by Westley, J. W., *Chemistry and Biochemistry of Amino Acids, Peptides and Proteins*, Vol. 1, Marcel Dekker, New York, New York, 1971, p. 1–21. A specific application to amines is described in Beckett, A. H. and Testa, B., *J. Chromatog.*, 69, 1972, p. 285.

In brief, a 1–5 mg. sample of the crystalline lasalocid salt of 1-amino-2-(3',4'-dimethoxyphenyl)propane which had precipitated was dissolved in methylene chloride and an aliquot thereof (0.05 mmol.) was treated with an equimolar amount of TPC reagent and 3 drops of triethylamine. The mixture was shaken for 1 minute and then 1 microliter was injected into a Hewlett Packard gas chromatograph. This apparatus, equipped with an elctronic integrator and fitted with a 2-m glass column, 3 mm i.d., was packed with 10% OV-17 on Gas-Chrom Q, 100–120 mesh. This packing comprises a 10% by weight amount of a 50% phenyl methyl silicone liquid on a silanized diatomaceous earth support. The operating conditions were:

Injector — 295° C.
Flame Ionization Detectors — 270° C.
Nitrogen flow — 30 ml./min.

The column operating temperature was 230° C. and the retention time of the SR and SS diastereoisomers were 39 and 42 minutes respectively.

The proportion of R to S enantiomer in the lasalocid amine salt was 35:65, i.e., an optical purity of 30%. Optical purity is defined as the difference between the percent of the major enantiomer and the minor enantiomer in the isolated lasalocid salt.

The crystals of the lasalocid salt were redissolved in methylene chloride and admixed with 24 ml. of ethanol. The solution was again left overnight at room temperature.

The resulting crystals were separated by filtration and had a ratio of R to S enantiomer of 10:90, i.e., an optical purity of 80%.

The crystals of the S(+)-1-amino-2-(3',4'-dimethoxyphenyl) propane salt of lasalocid were characterized as follows:

m.p. 185°–190° C.
[α]D −25° (C 1.0, $CHCl_3$)

(b) Conversion of the lasalocid salt of S(+)-1-amino-2-(3',4'-dimethoxyphenyl) propane to S(+)-1-amino-2-(3',4'-dimethoxyphenyl) propane hydrobromide 10 ml. of water containing 1 mmol HBr (0.1 N HBr) was thoroughly mixed with a solution of 770 mg. (0.98 mmol.) of the lasalocid salt of S(+)-1-amino-2-(3',4'-dimethoxyphenyl) propane in 10 ml. of methylene chloride. This lasalocid salt used had been isolated from the second recrystallization in step (a) above with 80% optical purity. The aqueous phase was separated and evaporated under reduced pressure.

The residue was taken up in ethanol. Crystallization therefrom yielded (+)-1-amino-2-(3',4'-dimethoxyphenyl) propane hydrobromide, m.p. 250° C., [α]D +26° (C 1.0, $H_2O$).

The absolute configuration was found to be S and the optical purity of the hydrobromide salt was 82% as determined by GLC of the N-trifluoracetyl-L-(S)-propyl (TPC) derivative. This configuration was confirmed by optical rotatory dispersion (ORD) using a Jasco J-20 automatic recording spectropolarimeter. Optical rotatory dispersion is a procedure wherein the optical rotation of a compound is measured over different wave lengths (e.g., 700 nanometers down to 200 nanometers).

(c) Isolation of R(−)-1-amino-2-(3',4'-dimethoxyphenyl)propane hydrobromide

The hydrobromide salt of R(−)-1-amino-2-(3',4'-dimethoxyphenyl) propane was isolated from the mother liquor after crystallization and removal by filtration of the lasalocid salt of S(+)-1-amino-2-(3',4'-dimethoxyphenyl) propane, by evaporation.

The residue from the above evaporation step was taken up in 10 ml. of methylene chloride and was thoroughly mixed with 10 ml. of an aqueous solution of 0.1 N HBr. The aqueous phase was separated and evaporated under reduced pressure. The residue was recrystallized from ethanol to yield R(−)-1-amino-2-(3',4'-dimethoxyphenyl) propane hydrobromide, m.p. 250° C.; [α]D −17.5° (C 1, H₂O).

The absolute configuration was shown to be R and the optical purity of the hydrobromide salt to be 82% as determined by GLC of the N-trifluoroacetyl-L-(S)-propyl (TPC) derivative. This configuration was confirmed by optical rotatory dispersion (ORD).

(d) Optical resolution of racemic 1-amino-2-(3',4'-dimethoxyphenyl) propane as a lasalocid salt using crystallization solvents other than ethanol The same technique used in Example (a) above to resolve 1-amino-2-(3',4'-dimethoxyphenyl) propane were repeated using n-hexane or ethyl acetate in place of ethanol as the crystallization solvent. The results are tabulated below.

Table 1

Efficiency of resolution of racemic 1-amino-2-(3',4'-dimethoxyphenyl) propane as a lasalocid salt using two different solvents for crystallization

| Crystallization Solvent | Number of Crystallizations | Ratio R:S | % Optical Purity |
|---|---|---|---|
| n-hexane | 1 | 34:66 | 32 |
| | 2 | 24:76 | 52 |
| ethyl acetate | 1 | 23:77 | 54 |
| | 2 | 15:85 | 70 |

EXAMPLE 2

(a) Optical resolution of racemic 1-amino-1-phenylethane 242 mg. of (2mmol.) of 1-amino-1-phenylethane, dissolved in 2 ml. of methylene chloride, were admixed with 1.18 g. (2 mmol.) of lasalocid dissolved in 4 ml. of methylene chloride. After 24 ml. of n-hexane were added to this mixture, the solution was left at room temperature overnight. As the methylene chloride evaporated, crystals formed from the concentrated solution. These crystals were separated by filtration to yield the lasalocid salts of 1-amino-1-phenylethane.

The optical purity, and, hence, the degree of discrimination between the enantiomers of the crystalline lasalocid salt of 1-amino-1-phenylethane was determined by Gas-Liquid Chromatography (GLC) analysis of its TPC derivative using, as in Example 1, a Hewlett Packard gas chromatograph equipped with an electronic integrator, fitted with a 2-m glass column, 3 mm i.d. which was packed with 5% DC-LSX on silanized Chromosorb W, 60-80 mesh. This column packing comprises 5% by weight of the DC-LSX liquid phase (50% trifluoropropyl, 1% vinyl methyl silicone) deposited on a silanized diatomaceous earth (Chromosorb W).

A 1-5 mg. sample of the crystalline amine salt which had precipitated was dissolved in methylene chloride and an aliquot thereof (0.05mmol.) was treated with an equimolar amount of TPC reagent and 3 drops of triethylamine. The mixture was shaken for 1 minute and then 1 microliter was injected into the gas chromatograph.

The column operating temperature was 185° C. and the retention time of the SR and SS diastereoisomeric TPC derivatives were 16 and 20 minutes respectively.

The proportion of R to S enantiomer in the crystallized lasalocid amine salt was 89:11, i.e., an optical purity of 78%.

The crystals of the lasalocid salt were redissolved in methylene chloride and admixed with 24 ml. of n-hexane. The solution was again left overnight at room temperature. The resulting crystals were separated by filtration and had a ratio of R to S enantiomer of 92:8, i.e. optical purity of 84%. The crystals were characterized as follows:

[α]D −77° (C 1, CHCl₃)
m.p. 198°–199° C.

Conversion of the lasalocid salt of R(+)-1-amino-1-phenylethane to the respective enantiomer, R(+)-1-amino-1-phenylethane, and recovery of S(−)-1-amino-1-phenylethane were accomplished by the procedures described in Examples 1(b) and 1(c) above.

(b) Optical resolution of racemic 1-amino-1-phenylethane as a lasalocid salt using crystallization solvents other than n-hexane The same technique used in (a) above to resolve 1-amino-1-phenylethane were repeated using ethyl acetate or ethanol instead of n-hexane as the crystallization solvent. The results are tabulated below after a single crystallization step.

Table 2

Efficiency of resolving of racemic 1-amino-1-phenylethane as a lasalocid salt on a single crystallization from two different solvents

| Solvent | Ratio R:S | % Optical Purity |
|---|---|---|
| Ethyl Acetate | 84:16 | 68 |
| Ethanol | 56:44 | 12 |

EXAMPLE 3

Optical Resolution of Other Primary Asymmetric Amines

Using techniques as described in Example 1 (a) and 2 (a) above, the following racemic amines were resolved:

1-amino-1-(4-bromophenyl)ethane
1-amino-1-naphthylethane
2-aminoheptane
tetrahydrofurfurylamine The preferred enantiomeric amine, on the basis of absolute configuration and sign of rotation, isolated in each case was R(+)-1-amino-1-(4-bromophenyl)ethane
R(+)-1-amino-1-naphthylethane
R(−)-1-aminoheptane
S(+)-tetrahydrofurfurylamine Optical purity was again determined by GLC with the following column operating temperatures and retention times of the SR and SS diastereoisomeric TPC derivatives of the four racemic amines.

| Amine | Temperature, °C. | Retention SR | Time SS |
|---|---|---|---|
| 1-amino-1-(4- | | | |

| Amine | Temperature, °C. | Retention SR | Time SS |
|---|---|---|---|
| bromophenyl) ethane | 205 | 19 | 24 |
| 1-amino-1-naphthylethane | 230 | 13 | 16.5 |
| 2-aminoheptane | 175 | 12 | 13.7 |
| tetrahydrofurfurylamine | 185 | 14 | 15 |

Table 3 lists the results obtained using n-hexane, ethyl acetate or ethanol as the solvent of crystallization.

Table 3

Efficiency of resoluton of four asymmetric amines as lasalocid salts using three different solvents

| Asymmetric Amine | Crystallization Solvent | Number of Crystallizations | Ratio R:S | Optical Purity, % |
|---|---|---|---|---|
| 1-amino-1-(4-bromo-phenyl) ethane | n-hexane | 1 | 86:14 | 72 |
| | | 2 | 91:9 | 82 |
| | | 3 | 100:0 | 100 |
| | ethyl acetate | 1 | 80:20 | 60 |
| | | 2 | 90:10 | 80 |
| | ethanol | 1 | 75:25 | 50 |
| | | 2 | 86:14 | 72 |
| 1-amino-1-naphthylethane | n-hexane | 1 | 72:28 | 44 |
| | | 2 | 92:8 | 84 |
| | ethyl acetate | 1 | 86:14 | 72 |
| | | 2 | 89:11 | 78 |
| | ethanol | 1 | 80:20 | 60 |
| | | 2 | 87:13 | 74 |
| 1-dimethylamino-1-phenyl-ethane | n-hexane | 2 | 10:90 | 50 |
| 2-aminoheptane | n-hexane | 1 | 81:19 | 62 |
| | | 2 | 86:14 | 72 |
| | ethyl acetate | 1 | 86:14 | 72 |
| | ethanol | 1 | 76:24 | 52 |
| tetrahydrofurfurylamine | n-hexane | 1 | 31:69 | 38 |
| | | 2 | 25:75 | 50 |

Conversions of the lasalocid salts to the respective enantiomeric amines; R(+)-1-amino-1-(4-bromophenyl)ethane, R(+)-1-amino-1-naphthylethane, R(−)-1-aminoheptane and S(+)-tetrahydrofurfurylamine and recovery of S(−)-1-amino-1-(4-bromophenyl)ethane S(−)-1-amino-1-naphthylethane, S(+)-1-aminoheptane and R(−)-tetrahydrofurfurylamine were accomplished by the procedures described in Example 1 (b) and (c) above.

The resolution by lasalocid of amines where the asymmetric center is separated by a methylene unit from the primary amino group, is not as efficient as the resolution of those amines wherein the asymmetric center was attached directly to the primary amino group. Moreover, the enantiomer which was preferentially crystallized in the primary amines where the asymmetric center was separated by a methylene unit from the primary amino group had the S absolute configuration in both cases whereas the enantiomer having the opposite absolute configuration was isolated in the primary amines where the asymmetric center was attached directly to the primary amino group. In the case of tertiary amines wherein the asymmetric carbon is attached directly to the tertiary amino group, the enantiomer which was obtained from the preferentially crystallized lasalocid salt has the S absolute configuration.

EXAMPLE 4

Since the lasalocid salt of R(+)-1-amino-1-(4-bromophenyl)-ethane had an optical purity of 100% after three crystallizations from methylene chloride/n-hexane (see Table 3), its conversion to the hydrochloride salt was undertaken.

1.58 grams (2 mmol) of the lasalocid salt of R(+)-1-amino-1-(4-bromophenyl)-ethane, isolated from the third crystallization from n-hexane, dissolved in 25 ml. of ethyl acetate were extracted twice with 25 ml. of 1N HCl. The aqueous extracts were combined and lyophilized to yield R(+)-1-amino-1-(4-bromophenyl)ethane hydrochloride, $[\alpha]D$ +2.6° (C 5, $H_2O$).

The hydrochloride was optically pure (R) as determined by GLC of the N-trifluoracetyl-L-(S)-prolyl (TPC) derivative.

Lasalocid was recovered quantitatively by evaporation of the ethyl acetate phase under reduced pressure.

EXAMPLE 5

1.49 g. (10 mmol.) of 1-dimethylamino-1-phenylethane, dissolved in 25 ml. of methylene chloride, were admixed with 5.9 grams (10 mmol.) of lasalocid in 25 ml. of methylene chloride. 100 ml. of n-hexane were added to this mixture and the resulting solution was left at room temperature overnight. As the methylene chloride evaporated, crystals formed from the concentrated solution. These crystals were separated by filtration and recrystallized from methylene chloride /n-hexane to yield the lasalocid salts of 1-dimethylamino-1-phenylethane.

1.3 grams of the lasalocid salt of 1-dimethyl-amino-1-phenylethane dissolved in 20 ml. of methylene chloride were extracted three times with 20 ml. of 1N HCl. The acid extracts were combined, dried over anhydrous sodium carbonate and concentrated to 232 mg. of an oil, (−)-dimethylamino-1-phenylethane$[\alpha]_D$ −62.4° (cl, isooctane).

The absolute configuration of the amine was found to be S by comparison with a standard sample of pure S(−)-dimethylamino-1-phenylethane which had an $[\alpha]_D$ −70° (cl, in octane). By comparing the $[\alpha]_D$ values of the resolved amine and the authentic S-isomer, the optical purity of the amine was estimated at 90%.

I claim:

1. In a process for resolving a racemic amine into its enantiomers by (a) forming a diastereomeric mixture of salts of the enantiomers of the racemic amine with an optically active acid component; (b) separating the diastereomers; (c) decomposing the salt of the desired enantiomer by treatment with a dilute aqueous acid and (d) recovering the desired enantiomer, the improvement which comprises utilizing lasalocid as the optically active acid component and, as the racemic amine, a primary asymmetric amine having its asymmetric center either attached directly to or separated by a single methylene unit from, the primary amino group, one optical isomer of which is preferentially crystallized as a salt of lasalocid.

2. The process of claim 1 wherein the amine is racemic 1-amino-1-phenylethane and the desired enantiomer is R(+)-1-amino-1-phenylethane.

3. The process of claim 1 wherein the primary amine is racemic 1-amino-1-(4-bromophenyl)ethane and the desired enantiomer is R(+)-1-amino-1-(4-bromophenyl)ethane.

4. The process of claim 1 wherein the primary amine is racemic 1-amino-1-naphthylethane and the desired enantiomer is R(+)-1-amino-1-naphthylethane.

5. The process of claim 1 wherein the primary amine is racemic 2-aminoheptane and the desired enantiomer is R(−)-2-amino-heptane.

6. The process of claim 1 wherein the primary amine is racemic tetrahydrofurfuryl-amine and the desired enantiomer is S(+)-tetrahydrofurfurylamine.

7. The process of claim 1 wherein the primary amine is racemic 1-amino-2-(3′,4′-dimethoxyphenyl)-propane and the desired enantiomer is S(+)-1-amino-2-(3′,4′-dimethoxyphenyl)-propane.

* * * * *